(12) United States Patent
Pilla et al.

(10) Patent No.: US 7,611,453 B2
(45) Date of Patent: Nov. 3, 2009

(54) APPARATUS AND METHOD FOR STATIC MAGNETIC FIELD TREATMENT OF TISSUE, ORGANS, CELLS, AND MOLECULES

(76) Inventors: Arthur A. Pilla, 1 Winding Ridge, Oakland, NJ (US) 07436; David John Muehsam, 12 Pompanuck Way, Cambridge, NY (US) 12816; Charles Zablotsky, 5821 Quiet Oak La., Ft. Lauderdale, FL (US) 33312; Ted Zablotsky, 44 Miamis Rd., West Hartford, CT (US) 06117

( * ) Notice: Subject to any disclaimer, the term of this patent is extended or adjusted under 35 U.S.C. 154(b) by 785 days.

(21) Appl. No.: 11/009,878

(22) Filed: Dec. 11, 2004

(65) Prior Publication Data

US 2005/0215842 A1  Sep. 29, 2005

Related U.S. Application Data

(60) Provisional application No. 60/529,213, filed on Dec. 12, 2003.

(51) Int. Cl.
*A61N 1/00* (2006.01)
(52) U.S. Cl. .......................................................... 600/15
(58) Field of Classification Search ............. 600/9–15; 607/45, 50, 51
See application file for complete search history.

(56) References Cited

U.S. PATENT DOCUMENTS

| 4,549,532 | A | 10/1985 | Baermann et al. |
| 5,441,495 | A * | 8/1995 | Liboff et al. ................. 600/9 |
| 5,450,858 | A | 9/1995 | Zablotsky et al. |
| 5,738,624 | A | 4/1998 | Zablotsky et al. |
| 5,965,282 | A | 10/1999 | Baermann et al. |
| 6,322,491 | B1 | 11/2001 | Bove et al. |
| 6,626,820 | B1 | 9/2003 | Ardizzone |

OTHER PUBLICATIONS

Weintraub, Michael, I. MD et al, Static Magnetic Field Therapy for Symptomatic Diabetic Neuropathy: A Randomized, Double-Blind, Placebo-Controlled Trial Arch Phys Med Rehabil vol. 84 May 2003, pp. 736-746.

* cited by examiner

*Primary Examiner*—Charles A Marmor, II
*Assistant Examiner*—Christine D Hopkins
(74) *Attorney, Agent, or Firm*—Leonard Taylor, Esq.

(57) ABSTRACT

An apparatus and method for static magnetic field treatment of plants, animals, and humans comprising the steps of configuring at least one composite static magnetic field by combining at least one of a bipolar static magnetic field and an axial static magnetic field, optimizing spatial distribution and amplitude of the composite static magnetic field at a target pathway structure by satisfying a mathematical model, and coupling the at least one optimized composite static magnetic field to the target pathway structure using a composite static magnetic device.

15 Claims, 6 Drawing Sheets

APPARATUS AND METHOD FOR STATIC MAGNETIC FIELD TREATMENT OF TISSUE, ORGANS, CELLS, AND MOLECULES

This application claims the benefit of U.S. Provisional Application 60/529,213 filed Dec. 12, 2003.

BACKGROUND OF THE INVENTION

1. Field of the Invention

This invention pertains generally to an apparatus and a method for therapeutically and prophylactically treating plants, animals and humans using static magnetic fields ("SMF") that are selected by optimizing spatial distribution and amplitude of a magnetic field at target pathway structures such as molecules, cells, tissues and organs. Another embodiment according to the present invention spatially configures SMF to satisfy Larmor precession conditions, so that treatment can be provided for relieving musculoskeletal pain, decreasing edema, increasing local blood circulation, to enhance healing, and to enhance wellbeing.

A preferred embodiment according to the present invention comprises juxtaposition of, for example, integrated, adjacent, contacting, permanent magnets of any shape having a bipolar portion that includes at least three juxtaposed circular portions of alternating polarity, beginning with north or south orientation in a central portion, and an axial portion having at least one polarity per face, whereby a first layer of the bipolar portion is connected to a first layer of the face of the axial portion. During a treatment session an embodiment according to the present invention of permanent magnets juxtaposed with a bipolar portion and an axial portion, produces an optimized magnetic field that can be positioned in proximity to target pathway structures, such as a molecules, cells, tissues, and organs, and can be directly applied to outer skin surfaces, through clothing, ice packs, heat packs, as well as being used in conjunction with compression and support wraps.

A preferred embodiment according to the present invention comprises a bipolar portion having juxtaposed opposite magnetic polarity portions, each magnetic polarity portion having about a 1 Gauss ("G") to 5000 G magnetic field amplitude at a surface of the bipolar portion, connected to an axial portion having about a 1 G to 5000 G magnetic field amplitude at the surface of the axial portion, whereby a resulting composite magnetic field is configured that can be applied to target pathway structures such as a molecules, cells, tissues and organs, for an exposure time of about 1 minute to about several hours per day. However, other exposure times can be used.

A preferred embodiment according to the present invention comprises a plurality of circular and rectangular axial portions and a plurality of circular and rectangular bipolar portions, the axial and bipolar portions having a surface area of at least about 1 $cm^2$, and a thickness of at least about 0.5 mm, whereby magnetic poles in the bipolar portion are produced in circular and annular zones. However, the magnetic poles can be configured in any zone shape, including random.

A preferred embodiment according to the present invention comprises at least one flexible permanent magnet constructed by incorporating ferrite particles into a biocompatible polymer whereby a synthetic material having rubber-like properties is formed that can be incorporated into anatomical wraps and supports for treatment of musculoskeletal aches, pains, and inflammation.

2. Discussion of Related Art

Static magnetic fields in a range of about 1 G to about 5000 G have significant therapeutic and prophylactic benefits, particularly for treatment of pain and edema from musculoskeletal injuries and pathologies.

At a molecular level, when a target pathway structure is in a receptive metabolic state such as that caused by injury, ambient range fields less than or equal to 2 G modulated calcium ("Ca+") binding to calmodulin ("CaM") which accelerated phosphorylation of a muscle contractile protein in a cell-free enzyme assay mixture. This has also been shown for CaM dependent cyclic nucleotide phosphodiesterase activity by modulating Ca+/CaM binding with a 2 G field. Magnetic fields ranging from about 23 G to about 3500 G have altered electrical properties of solutions as well as their physiological effects. At a cell level, a magnetic field of about 300 G doubled alkaline phosphatase activity in osteoblast-like cells. Fields between about 4300 G and about 4800 G significantly increased turnover rate and synthesis of fibroblasts. Neurite outgrowth from embryonic chick ganglia was significantly increased using magnetic fields of about 225 G to 900 G. Rat tendon fibroblasts exposed to a magnetic field of about 2.5 G showed extensive detachment of pre-attached cells, as well as a temporarily altered morphology. A minimum magnetic field gradient of about 15 G/mm was shown to cause approximately 80% action potential blockade in an isolated nerve preparation. A rabbit model demonstrated that 10 G fields could significantly affect cutaneous microcirculation and could cause a biphasic response dependent upon a pharmacologically determined state of a target pathway structure.

Therapeutic and prophylactic treatment with magnets has produced varied results. Although a necklace having small 1300 G magnets had no influence on chronic neck and shoulder pain, pain was reduced in post-polio patients by 76% for a single 45 minute treatment in which bipolar magnets having alternating poles per face and a magnetic field of about 300 G to about 500 G, were applied to pain pressure trigger points, and not directly on a pain site. A magnetic foil having no field level reported was added to a molded insole designed for treatment of plantar foot pain. The magnetic foil had no effect on plantar heel pain syndrome. Pads having arrays of ceramic magnets having magnetic fields of about 150 G to about 400 G and a single pole per face were placed over a liposuction site immediately post operative and left in place for 14 days. Discoloration, edema and pain were reduced by 40%-70% over 7 days post suction lipectomy. Arrays of magnets in mattress pads that were either single-pole per face or alternating poles per face confirmed significant pain reduction. The outcome measures of fibromyalgia such as pain and sleep disorders, were reduced by approximately 40% in patients who slept on a mattress pad containing arrays of ceramic magnets having magnetic fields of about 800 G and a single pole per face, over a 4 month period. Only the ceramic magnets provided sufficient magnetic dosage to significantly reduce pain from fibromyalgia. Approximately 90% of patients with diabetic peripheral neuropathy received significant relief of pain, numbness and tingling using alternating pole magnetic insoles having a magnetic field of 475 G. Only 30% of non-diabetic subjects showed equivalent improvement using the same insoles. Chronic lower back pain was not affected by application of a pad having a geometric array of alternating pole 300 G magnetic fields applied over a lumbar region for 6 hrs/day, 3 times per week for one week, even though the magnets used have been shown to deliver a sufficient magnetic field dose to deep tissue sites in the lower back. Peripheral blood circulation in healthy individuals was not affected by 500 G SMF. Chronic pelvic pain and disability were significantly decreased using about 300 G to about 500 G bipolar magnets arranged in concentric circles, over pain pressure trigger points. Shoe insoles having 450 G multipolar magnets significantly reduced neuropathic pain and increased quality of life in patients with symptomatic diabetic peripheral neuropathy. The effective magnetic field from the shoe insole surface was reported to extend to 20 mm with 250 G at 1 mm, 90 G at 3 mm, 1.5 G at 13 mm and equal to the earth's field at 20 mm.

Several models have been put forth analyzing effects of electromagnetic fields ("EMF") on charged ions and ligands due to a magnetic Lorentz force. Early models treated electromagnetic field effects on ion binding to proteins on a surface of a cell. An action of electric and magnetic forces on different ionic messengers and binding sites via a Lorentz equation, describes motion of a charged particle in a magnetic field subject to constraints due to a molecular and thermal noise environment. Magnetic fields of about 1 Gauss to about 10 Gauss have been shown to affect ion/ligand binding in presence of thermal noise for sufficiently long bound lifetimes, about 1 second or longer, such as occur in $Ca^{2+}$/CaM binding which is involved in a wide range of physiologically significant biochemical cascades related to tissue growth and repair. In a cellular environment, weak magnetic field effects via the Lorentz force can only be expected for a bound phase of the ion/ligand trajectory. Collision frequencies that occur, such as with other ions and water molecules in bulk water or in an ion channel, in all other phases of a trajectory require minimum effective field strengths in a Tesla range to be detectable when thermal noise is present. That range is clearly well above fields at which therapeutic and prophylactic static magnetic field effects have been demonstrated, indicating that a primary transduction target for therapeutic and prophylactic static magnetic field effects is a bound ion.

Theories exist that attempt to explain how magnetic field treatment interacts with a target pathway structure. The theories range from Lorentz force effects on bulk ion/charge movement, direct effects on blood flow, and direct effects on movements of charges at biological surfaces. However, it can be shown that the magnetic field levels of about 1 G to about 5000 G that are generally used in therapeutic and prophylactic magnets are too small to produce these effects, primarily because of thermal noise.

An embodiment according to the present invention comprises a Larmor precession mechanism that relates to an effect of SMF on dynamic movement of a bound charge. This advantageously allows relatively low amplitude SMF to be detected since bound charges are largely shielded from thermal noise effects.

SMF in various configurations has been used for treatment of musculoskeletal pain. Therefore a need exists for configuring SMF for optimal dosage for therapeutic and prophylactic purposes according to Larmor precession.

SUMMARY OF THE INVENTION

An apparatus and method of delivering a static magnetic field to human, animal and plant molecules, cells, tissues, and organs for therapeutic and prophylactic purposes. Particularly, an embodiment according to the present invention comprises a permanent magnet having both axial and bipolar properties, such that the magnet produces a resulting magnetic field that can penetrate into a treatment area while providing significant three dimensional ("3D") magnetic field gradients. This magnetic field configuration advantageously allows a stimulus to be applied to molecules, cells, tissues, and organs by coupling to a Larmor precession of bound ions and ligands at regulatory molecules in physiologically significant biochemical cascades. A preferred embodiment according to the present invention is a flexible ferrite permanent magnet having a magnetic field of about 1 G to about 5000 G amplitude including a first portion comprising alternating circular positive and negative poles and an integrated second portion comprising an axial magnetic field with a north pole or a south pole facing the first portion. An object of the present invention is to satisfy Larmor precession conditions by configuring a composite axial/bipolar magnet to produce a magnetic field having a spatial amplitude distribution thus advantageously allowing it to be both at right angles to randomly oriented axes of vibration of bound charges, and large enough to be detectable according to known kinetics of ion and ligand binding in physiologically relevant biochemical cascades. Other embodiments according to the present invention include bipolar magnets of any shape and any pole/field pattern configuration integrated with an axial magnet of any shape. A preferred embodiment according to the present invention comprises juxtaposition of one layer of axial and one layer of bipolar flexible plastic magnets. However, other embodiments according to the present invention can comprise any combination of types of magnets such as ferrite, ceramic, rare earth, and electromagnets. An embodiment according to the present invention can also be used in conjunction with anatomical supports for relief of musculoskeletal pain.

The above and yet other objects and advantages of the present invention will become apparent from the hereinafter set forth Brief Description of the Drawings, Detailed Description of the Invention, and Claims appended herewith.

BRIEF DESCRIPTION OF THE DRAWINGS

Preferred embodiments of the present invention will be described below in more detail, with reference to the accompanying drawings.

DETAILED DESCRIPTION

In a preferred embodiment according to the present invention SMF modulates precessional motion at a characteristic Larmor frequency in a polarized ion/water complex that is present at an electrified interface of an ion/ligand binding site. This modulates thermal fluctuations in bound ion/water orientation angles, thereby affecting dynamics of a dielectric constant at the binding site that facilitates passage of an ion to and from an outer Helmholtz plane that is unbound, and facilitates passage of an ion to and from an inner Helmholtz plane that is bound, producing a resultant modulation of ion binding kinetics. A minimum threshold for magnetic field effects on ion/water orientation in the presence of thermal noise of about a 0.1 µT to about 1 µT range where T=Tesla=$10^4$ G, will occur, based upon lifetime of binding in the about 0.001 to about 1.0 second time range at a molecular cleft. These magnetic field effects occur for field strengths well below a threshold for which direct Lorentz force effects on ion trajectories occur when thermal noise is present. For direct Lorentz force effects this threshold lies in a mT range for an extreme low viscosity target pathway structure with few collisions, and can be as high as $10^7$ T for a fully hydrated ion experiencing significantly more thermal collisions. It can be shown that both coherent and thermal components of an ion at a binding site exhibit Larmor precession when an applied magnetic field is present. In addition, even in the absence of initial conditions resulting in a coherent component, as the amplitude of the thermal component grows oscillator orientation precesses at a Larmor frequency in a plane perpendicular to an applied magnetic field direction. Larmor mechanics converts magnetic field amplitude into a precessional frequency determined by a gyromagnetic ratio of a target pathway structure. Each Larmor precession frequency determines a time to reach favored orientations at a binding interface, or rate a which favored orientations are reached, thus modulating a binding rate constant.

A Larmor precession mechanism for SMF bioeffects requires that a target pathway structure charge must be bound for times exceeding a millisecond range, and a magnetic field must have an amplitude component sufficient to induce precession oriented at right angles to an original axis of vibration of a target pathway structure. A relevant target pathway structure has been shown to be $Ca^{2+}$ bound at CaM. A $Ca^{2+}$/CaM system is involved in regulatory cascades relevant to growth factor and cytokine release from cells responding to growth and repair signals in living systems. Tests of an embodiment according to the present invention using Ca/CaM dependent myosin phosphorylation showed that SMF having field strengths as low as 1 G could significantly increase phosphorylation, by up to 2× dependent upon initial $Ca^{2+}$ concentration.

A Larmor precession model demonstrates that precessional motion at a Larmor frequency of charged particles such as ions/ligands and water that are bound inside a binding site or molecular cleft, can be modulated by applied magnetic fields to affect binding kinetics. Precession introduces coherence into thermal fluctuations of bound ion/water orientation angles, modulating a rate at which orientations favoring binding/dissociation are reached. This coherence modulates fluctuations of a dielectric constant at a binding site, thus facilitating passage of an ion/ligand to or from an unbound state and from or to a bound state. The model shows a threshold of about a 0.1 µT (0.001 G=1 mG) to about 1 µT (0.01 G=10 mG) range for magnetic field effects on kinetics of ion binding when thermal noise is present for bound times approaching a second range. A Larmor model also shows that a magnetic field effect will saturate at relatively low values of a magnetic field that correspond to precession frequencies within a binding time constant frequency range.

A static magnetic field couples to a binding process by altering precession frequencies of bound ions. For fields in a mT range, bound lifetime must be sufficiently long for example greater than 1 msec, to establish a thermal noise threshold. Rotational degrees of freedom should also exist, such as those found for ions/water bound in the molecular clefts of macromolecules. A Larmor precession frequency can be expressed as:

$$\omega_L = -\Gamma B,$$

where $\omega_L$ is a Larmor frequency, $\Gamma$ is a gyromagnetic ratio of the system and B is a magnetic field amplitude. Generally, a gyromagnetic ratio will be a 3×3 matrix yielding dipole moment from molecular dynamics. Thus a Larmor frequency for water molecule precession is a complicated function of system parameters, specific to a particular structure of each particular target pathway structure.

Larmor precession effectively converts magnetic field amplitude into a frequency determined by a gyromagnetic ratio, such as a function of charge and mass of a bound particle, of a hydrated target pathway structure. Each Larmor precession frequency determines time to reach favored orientations, resulting in a modulation of ion binding kinetics via a time constant defined in an electrical equivalent circuit analog for binding. Thus, magnetic fields may couple with binding kinetics via a Larmor frequency in a manner analogous to that described for electric field effects on ion binding. A binding process can be illustrated as a dynamic system wherein a particle has two energetically stable points separated by a few kT such as a double potential well, either bound in a molecular cleft, or unbound in a plane of closest approach such as a Helmholtz plane, at an electrified interface between a molecular cleft and its aqueous environment. Ion binding/dissociation can then be treated as a process of hopping between two states and EMF effects are measured by modulation of a ratio of time bound in a molecular cleft to time unbound in a Helmholtz plane. A reaction coordinate q(t) subject to inertia and a damping force proportional to dq/dt can be defined. A potential energy function $V(q,\omega_L)$ can be modified either directly by an induced electric field, or indirectly by a static magnetic field via its effect on Larmor precession. Thermal noise, $F_{noise}$, is a driving force for ion binding and dissociation. Such a system can be described by a differential equation as:

$$\frac{d^2q}{dt^2} + \eta\frac{dq}{dt} + \frac{dV(q, \omega_L)}{dq} = F_{noise}$$

where η is a coefficient of damping, t is time.

In a static magnetic field Larmor frequency is a rate at which an instantaneous local dielectric constant reaches extrema favoring binding kinetics. Higher Larmor frequencies due to stronger magnetic fields, increase this rate. A potential energy function $V(q,\omega_L)$ is thus dependent on a Larmor frequency such as static magnetic field amplitude via:

$$V(q) = \alpha_1 \frac{q^4}{4} - \alpha_2 \frac{q^2}{2} + qC(F_{noise}),$$

where the nonnegative coefficients $\alpha_1$, and $\alpha_2$, are characteristic of the receptor molecule-hydration binding kinetics and C is an appropriate constant determined by experiment. A potential energy function $V(q,\omega_L)$ describes a double well potential wherein potential energy wells correspond to bound and unbound states, and effect of a magnetic field is to modulate relative depth of wells via Larmor precession.

A Larmor precession model can be applied to $Ca^{2+}$-calmodulin dependent myosin phosphorylation that is EMF sensitive for $Ca^{2+}$-depleted conditions and during a nonequilibrium phase of a reaction. Kinetics favor a bound state according to $k_{on}/k_{off} \cong 10^2$-$10^3$, an instantaneous exchange reaction rate is dependent upon instantaneous free $[Ca^{2+}(t)]$, and phosphorylation increases for increasing $[Ca^{2+}(t)]$. An embodiment according to the present invention of a Larmor precession model shows that $[Ca^{2+}(t)]$ is proportional to a ratio of time an ion is free for example unbound, to the time the ion is bound:

$$[Ca^{2+}(t)] = \rho \frac{t_{free}}{t_{bound}}.$$

where $\rho$ is a proportionality constant. An applied magnetic field thus modulates $[Ca^{2+}(t)]$, causing an increase in instantaneous reaction rate, such as an increase in net bound $Ca^{2+}$. Increasing field strength increases Larmor frequency further favoring a free state in a double-well potential energy function. An increase in a ratio of time free/bound for increasing field, and resulting increase in $[Ca^{2+}(t)]$ can yield a corresponding increase in enzyme kinetics.

Figure 1:
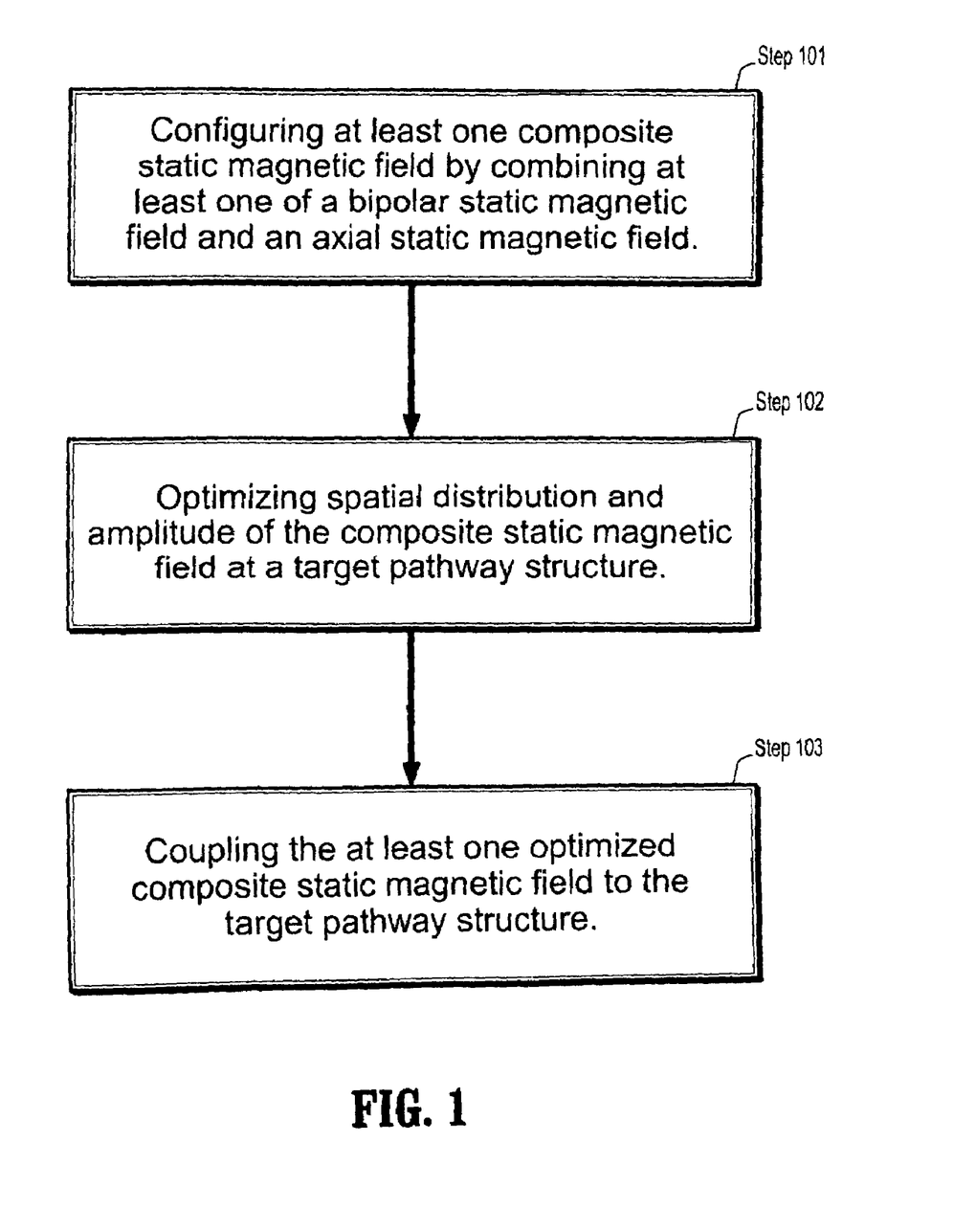
FIG. 1 is a flow diagram of a method for static magnetic field treatment of plant, animal, and human target pathway structures such as tissues, organs, cells, and molecules according to an embodiment of the present invention.

Referring to FIG. 1, at least one composite static magnetic field is configured by combining a bipolar magnetic field and an axial magnetic field (Step 101). In a preferred embodiment according to the present invention a bipolar magnetic field can be configured by comprising alternating circular positive and negative poles and an integrated second portion comprising an axial magnetic field having a north pole or south pole facing the first portion. Once a composite static magnetic field is configured its spatial distribution and amplitude at a target pathway structure such as a molecule, cell, tissue, and organ, are optimized by applying a Larmor precession model (Step 102). Larmor precession converts magnetic field amplitude into a frequency determined by a gyromagnetic ratio of the target pathway structure. During treatment of a target pathway structure, the optimized composite static magnetic field is coupled to the target pathway structure by altering precession frequencies (Step 103).

Figure 2A:
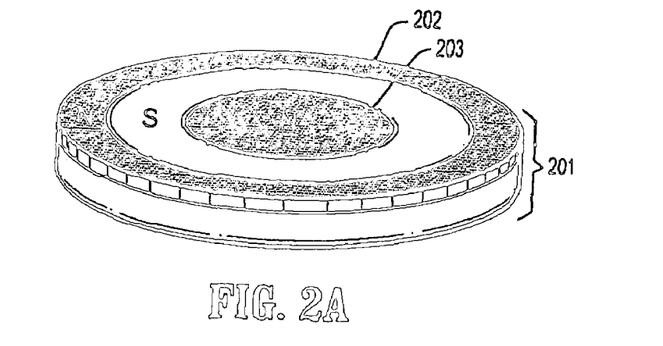
FIG. 2A is a view of a magnetic field having a bipolar portion configured according to a preferred embodiment of the present invention.
Figure 2B:
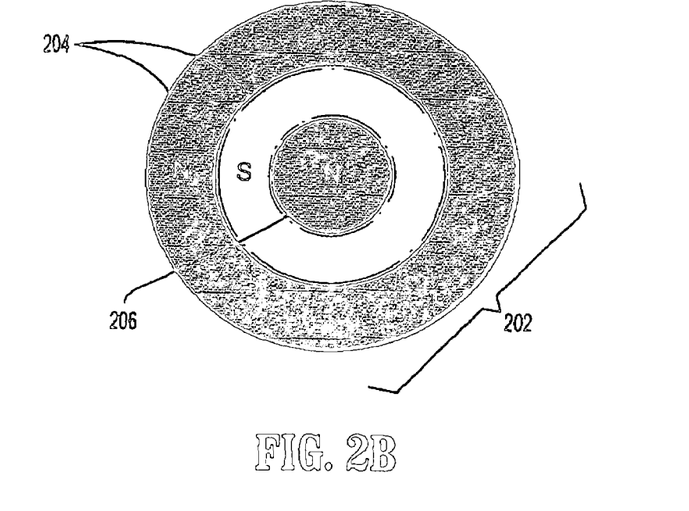
FIG. 2B is a view of a magnetic field having an axial portion configured according to a preferred embodiment of the present invention.
Figure 2C:
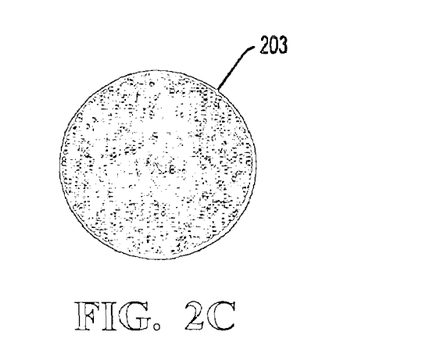
FIG. 2C is a view of a magnetic field having a bipolar portion and an axial portion configured according to a preferred embodiment of the present invention.

Referring to FIGS. 2A, 2B, and 2C a preferred embodiment according to the present invention of a composite magnet is illustrated. Crosshatched areas in FIGS. 2A, 2B, and 2C represent north pole orientation but other orientation configurations can be used. A composite magnet 201 having a bipolar portion 202 and an axial portion 203 is shown. The composite magnet 201 can be assembled using any method known to persons skilled in the art. In FIG. 2B, the bipolar portion 202 comprises alternating magnetic polarities 204 as annuli juxtaposed to a central circular portion 206. South pole orientation is on an opposite facing plane (not shown in FIG. 2C). A preferred embodiment according to the present invention of a composite magnet comprises a circular configuration having a diameter between about 3 cm to about 25 cm and a thickness between about 0.5 mm and to about 2 mm. However each portion of the composite magnet can be configured differently whereby any geometric shape can be formed, including random shapes.

Figure 3A:
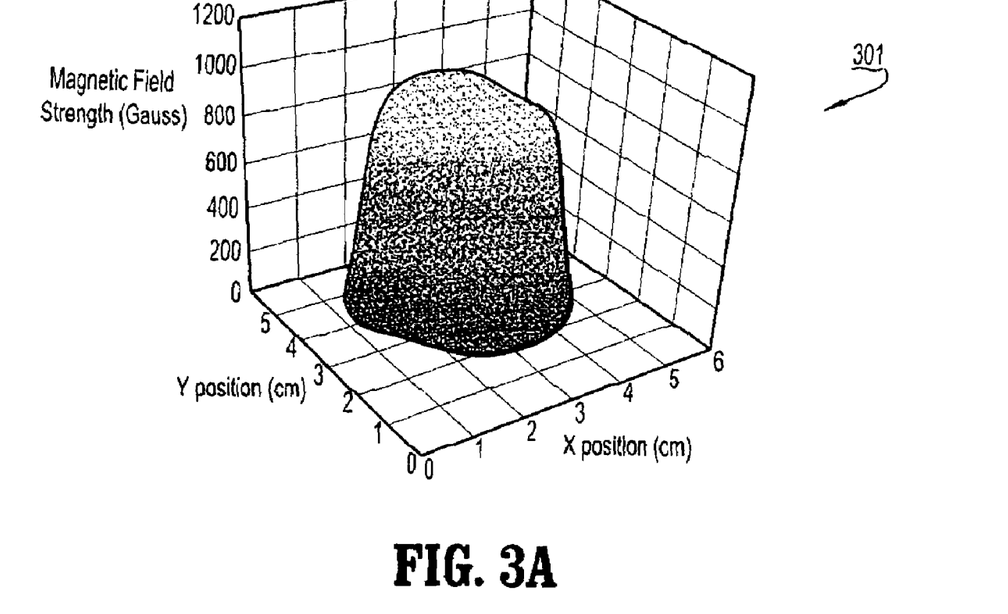
FIG. 3A is a 3D graphical illustration of a spatial configuration of a magnetic field of an axial portion of a magnet according to a preferred embodiment of the present invention.
Figure 3B:
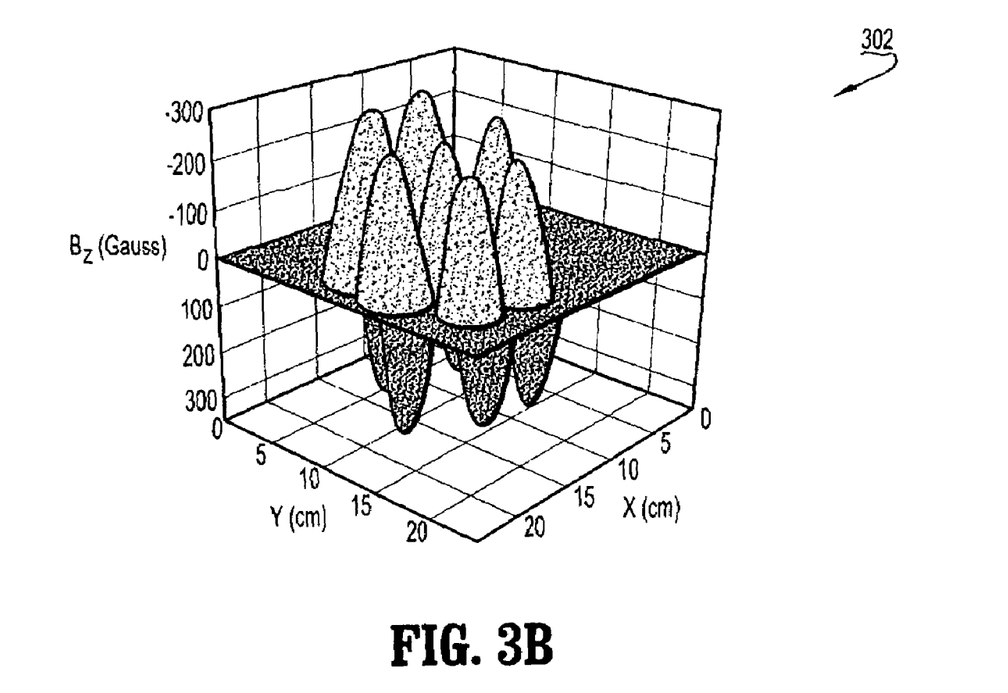
FIG. 3B is a 3D graphical illustration of a spatial configuration of a magnetic field of a bipolar portion of a magnet according to a preferred embodiment of the present invention.

Referring to FIG. 3A, a graphical spatial configuration of a magnetic field emanating from an axial portion 301 of a magnet according to a preferred embodiment of the present invention, is shown. FIG. 3B depicts a graphical spatial configuration of a magnetic field emanating from an bipolar portion 302 of a magnet according to a preferred embodiment of the present invention. The spatial distribution of a magnetic field in a bipolar portion 302 illustrates a manner by which a magnetic field passes from positive to negative orientation thereby creating at least one magnetic field gradient. The spatial distribution of the magnetic field in an axial portion 301 shows an absence of multiple gradients and is typical for a standard magnet having a single pole per face. A combination of the spatial orientations shown in FIG. 3a and FIG. 3b allows static magnetic field components along x, y or z axes to be applied with sufficient amplitude to an ion/ligand binding target pathway structure to be detectable, thereby satisfying a Larmor precession model. A preferred embodiment according to the present invention can configure magnets using combinations of spatial distributions other than those shown in FIG. 3a and FIG. 3b to satisfy a Larmor model. Another embodiment according to the present invention includes juxtaposition of an axial magnet with a bipolar magnet having any pole pattern and shape.

Figure 4:
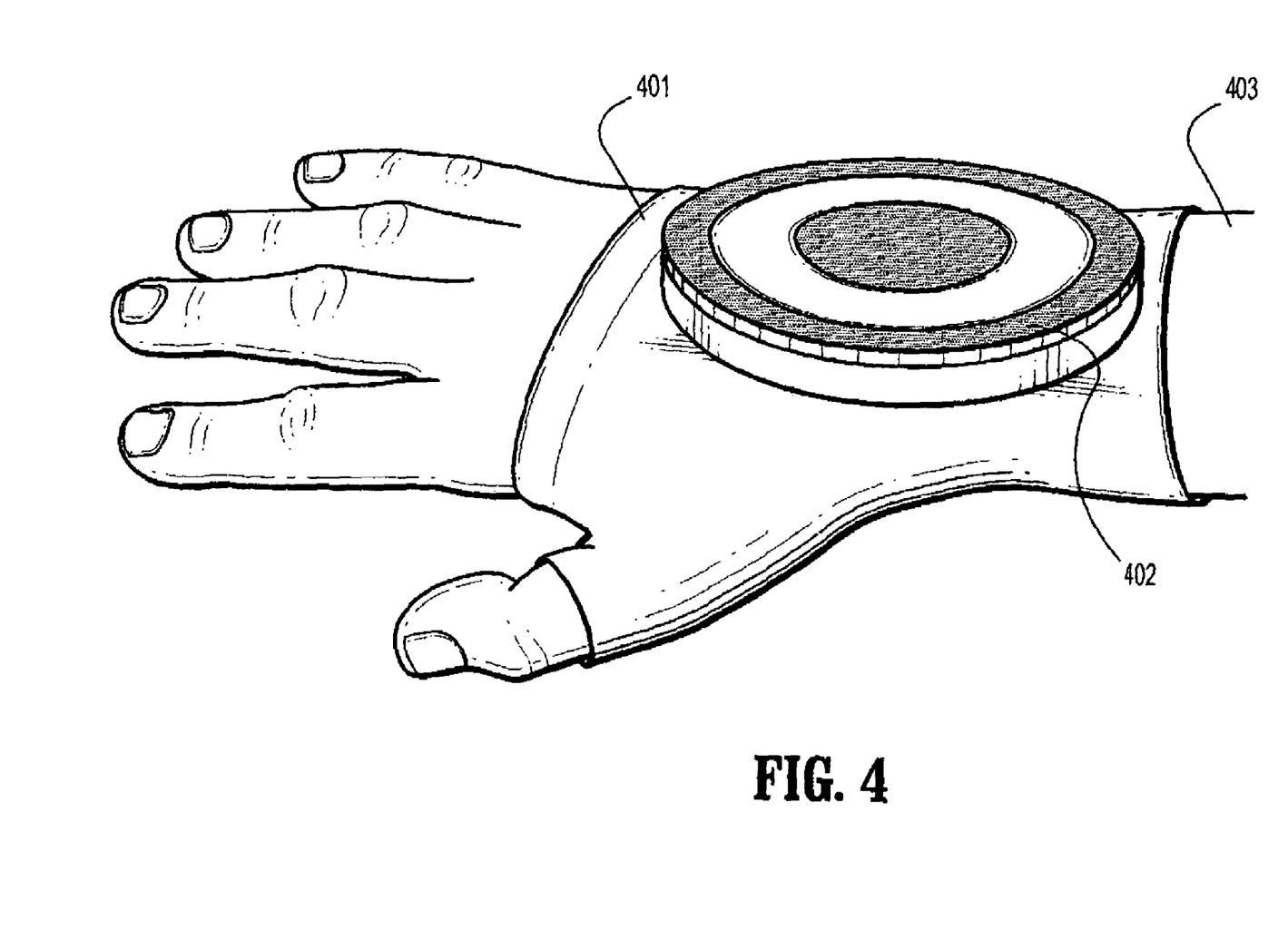
FIG. 4 is a view of a positioning device such as a wrist support according to a preferred embodiment of the present invention.

FIG. 4 shows a wrist support 401 according to a preferred embodiment of the present invention. The wrist support 401 can be made of any anatomical or support material such as neoprene. A magnet 402 can be incorporated into wrist support 401 for example by stitching. The magnet 402 can also be affixed onto the wrist support 401 by a fastening device such as Velcro® (not shown). The magnet 402 can also be held in place by a wrist support 401 made of an elastic material (not shown). Magnetic field orientation according to a preferred embodiment of the present invention, is applied from a dorsal that is top portion, to a plantar that is bottom portion, of a wrist 403. The magnetic field orientation can also be achieved with a plurality of magnets placed at anatomically relevant positions for a desired therapeutic and prophylactic outcome. Although a wrist support is depicted as a preferred embodiment according to the present invention, other embodiments include but are not limited to, incorporation of a composite magnet in an anatomical wrap or anatomical support designed for any portion of a human or animal anatomical location. For example, an embodiment according to the present invention can be incorporated in mattresses, mattress pads, pillows, apparel, footwear, knee, elbow, lower back, and shoulder wraps and supports.

Example 1

Figure 5:
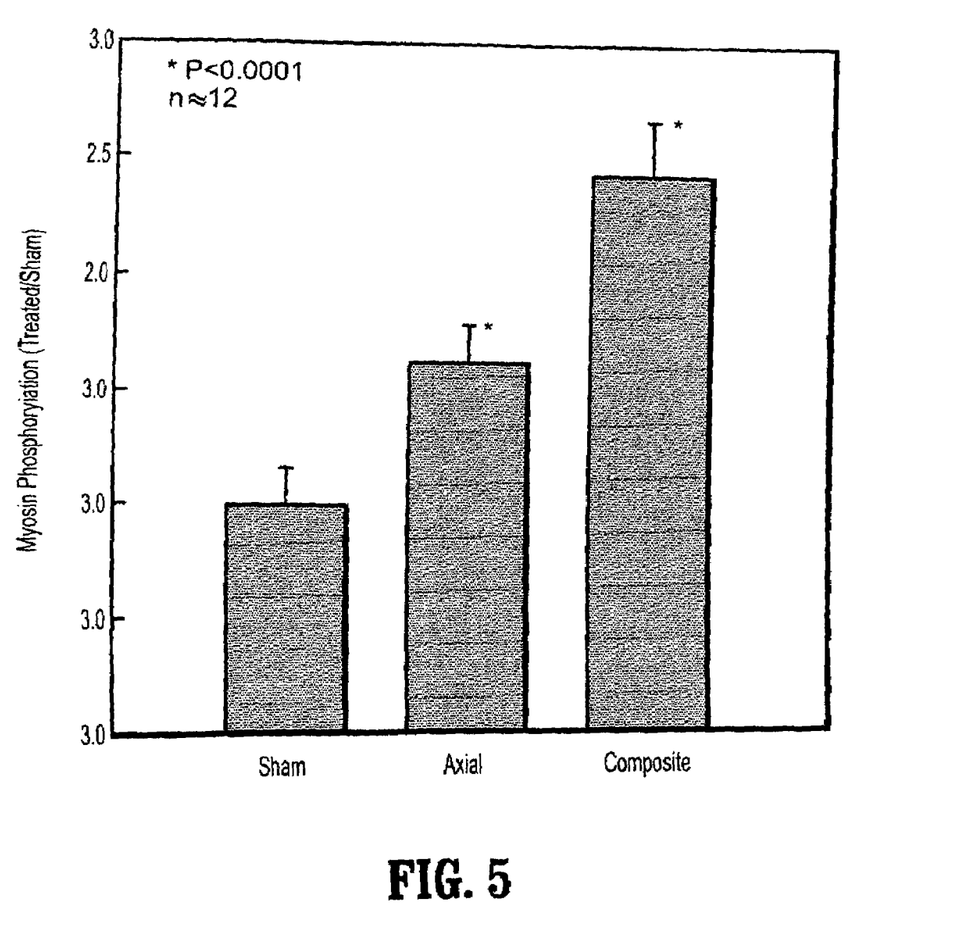
FIG. 5 is a bar chart illustrating that a composite magnet has a significantly greater effect on $Ca^{2+}$, as measured by myosin phosphorylation according to an embodiment of the present invention.

Effects of a magnetic field configured using an embodiment according to the present invention versus a standard axial magnet have been tested on a myosin phosphorylation enzyme assay system. A cell-free reaction mixture was chosen for phosphorylation rate to be linear in time for several minutes, and to be rate limited by $Ca^{2+}$. The reaction mixture consisted of 40 mM Hepes buffer, pH 7.0; 0.5 mM magnesium acetate; 1 mg/ml bovine serum albumin; 0.1% (w/v) Tween 80; 1 mM EGTA; 70 nM CaM; 160 nM MLC and 2 nM MLCK. Free $Ca^{2+}$ was varied in a about 1 μM to about 7 μM range. A low MLC/MLCK ratio was chosen to obtain linear time behavior in a minute range. The reaction mixture was aliquoted in 100 µL portions into 1.5 ml Eppendorf tubes, placed in a specially designed water bath maintained at 37±0.1° C. The reaction was initiated with 2.5 µM $^{32}P$ ATP, and was stopped with Laemmli Sample Buffer solution containing 30 µM EDTA. Phosphorylation was allowed to proceed for 5 min and was evaluated by counting $^{32}P$ incorporated into myosin light chains. A magnetic exposure system comprised either an axially magnetized or composite axial plus bipolar magnet. Both magnets had a resultant field of 20 G at a target pathway structure site, however the composite magnet was constructed to have significantly more field gradients to satisfy Larmor precession requirements. Results are shown in a bar chart in FIG. 5, wherein it can be seen that a composite magnet according to an embodiment of the present invention, had a significantly greater effect on $Ca^{2+}$, as measured by myosin phosphorylation.

Example 2

Figure 6:
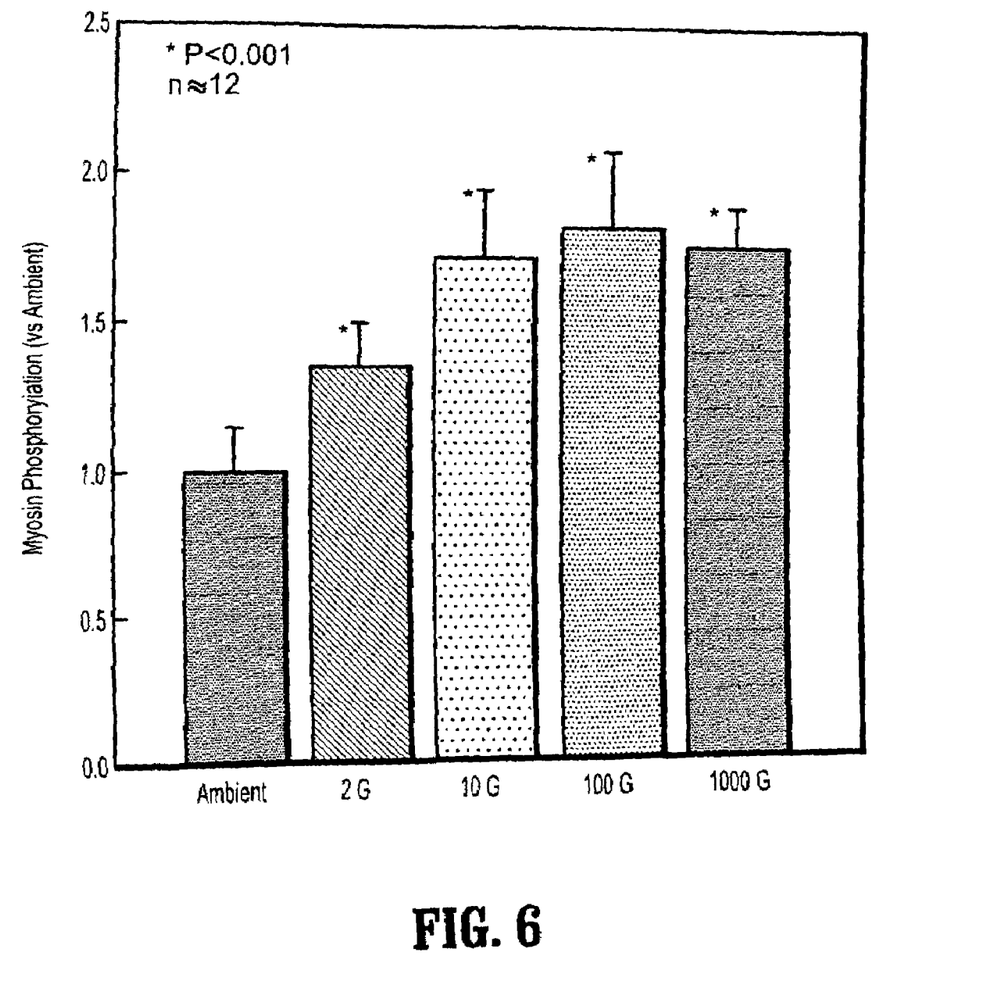
FIG. 6 is a bar chart illustrating that static magnetic field effects saturate when precession frequency approaches an ion binding time constant of a target pathway structure according to an embodiment of the present invention.

In another series of experiments a Larmor precession model demonstrated that static magnetic field effects would saturate when precession frequency which is directly proportional to magnetic field strength, approaches an ion binding time constant of a target pathway structure. A myosin phosphorylation system was used as described above in Example 1. Results are shown in a bar chart in FIG. 6, wherein it can be seen that an acceleration of $Ca^{2+}$ binding at calmodulin saturates at approximately 10 G that corresponds to a precession frequency of about 1 kHz, that is at a $Ca^{2+}$ binding time constant for calmodulin.

Having described embodiments for an apparatus and a method for static magnetic field treatment of plants, animals, and human target pathway structures such as molecules, cells, tissues, and organs, it is noted that modifications and variations can be made by persons skilled in the art in light of the above teachings. It is therefore to be understood that changes may be made in the particular embodiments of the invention disclosed which are within the scope and spirit of the invention as defined by the appended claims.

What is claimed is:

1. A method for static magnetic field treatment of plants, animals, and humans comprising the steps of:
   configuring at least one composite static magnetic field by combining at least one of a bipolar static magnetic field and an axial static magnetic field;
   optimizing spatial distribution and amplitude of said composite static magnetic field at a target pathway structure by satisfying a mathematical model wherein said mathematical model includes a Larmor precession model; and
   coupling said at least one optimized composite static magnetic field to said target pathway structure using a composite static magnetic device.

2. The method of claim 1, wherein said step of optimizing spatial distribution and amplitude of said composite static magnetic field further comprises optimizing a peak composite static magnetic field to be between about 0.1 G and about 5000 G.

3. The method of claim 1, wherein said step of optimizing spatial distribution and amplitude of said composite static magnetic field further comprises optimizing a composite static magnetic field gradient to be between about 0.1 G/mm and about $10^6$ G/mm.

4. The method of claim 1, wherein said step of optimizing spatial distribution and amplitude of said composite static magnetic field further comprises optimizing a composite static magnetic field gradient to be between about 0.1 G/mm and about $10^6$ G/mm, whereby said composite static magnetic field gradient is applied to a treatment volume of at least about 0.1 $mm^3$.

5. The method of claim 1, wherein said step of optimizing spatial distribution and amplitude of said composite static magnetic field further comprises optimizing a peak composite static magnetic field to be between about 0.1 G and about 5000 G, whereby said peak composite static magnetic field is applied to a treatment volume of at least about 0.1 $mm^3$.

6. The method of claim 1, wherein said target pathway structure includes at least one of a molecule, a cell, a tissue and an organ.

7. The method of claim 1, wherein said step of coupling said at least one optimized composite static magnetic field further comprises coupling said at least one optimized composite static magnetic field to reduce pain.

8. The method of claim 1, wherein said step of coupling said at least one optimized composite static magnetic field further comprises coupling said at least one optimized composite static magnetic field to reduce edema.

9. The method of claim 1, wherein said step of coupling said at least one optimized composite static magnetic field further comprises coupling said at least one optimized composite static magnetic field to enhance healing.

10. The method of claim 1, wherein said step of coupling said at least one optimized composite static magnetic field further comprises coupling said at least one optimized composite static magnetic field to enhance wellbeing.

11. The method of claim 1, wherein said step of coupling said at least one optimized composite static magnetic field further comprises coupling said at least one optimized composite static magnetic field to use in combination with at least one of standard and nonstandard medical therapies.

12. The method of claim 1, wherein said step of coupling said at least one optimized composite static magnetic field further comprises coupling said at least one optimized composite static magnetic field to use in combination with at least one of standard and nonstandard physical therapies.

13. The method of claim 1, wherein said step of coupling said at least one optimized composite static magnetic field further comprises using a positioning device to deliver for treatment said at least one optimized composite static magnetic field to said target pathway structure.

14. The method of claim 13, wherein said positioning device includes at least one of anatomical supports, anatomical wraps, mattresses, mattress pads, pillows, and apparel.

15. The method of claim 14, wherein said apparel includes garments, fashion accessories, and footwear.

* * * * *